United States Patent

Matusz et al.

[11] Patent Number: 5,380,697
[45] Date of Patent: Jan. 10, 1995

[54] ETHYLENE OXIDE CATALYST AND PROCESS

[75] Inventors: Marek Matusz, Houston, Tex.; Carolus M. A. M. Mesters, Amsterdam, Netherlands; John E. Buffum, Houston, Tex.

[73] Assignee: Shell Oil Company, Houston, Tex.

[21] Appl. No.: 118,486

[22] Filed: Sep. 8, 1993

[51] Int. Cl.⁶ .................... B01J 21/04; B01J 23/30
[52] U.S. Cl. .................... 502/348; 502/216; 502/300; 502/313; 502/344; 502/353; 549/534
[58] Field of Search ............. 502/344, 347, 348, 355

[56] References Cited

U.S. PATENT DOCUMENTS

| | | | |
|---|---|---|---|
| 3,316,279 | 4/1967 | Fenton | 260/348.5 |
| 3,702,259 | 11/1972 | Nielsen | 117/37 R |
| 3,844,981 | 10/1974 | Cusumano | 252/471 |
| 3,962,136 | 6/1976 | Nielsen et al. | 252/454 |
| 3,962,285 | 6/1976 | Cusumano | 260/348.5 R |
| 3,972,829 | 8/1976 | Michalko | 252/430 |
| 4,005,049 | 1/1977 | Fields | 252/467 |
| 4,010,115 | 3/1977 | Nielsen et al. | 252/454 |
| 4,012,425 | 3/1977 | Nielsen et al. | 260/348.5 R |
| 4,356,312 | 10/1982 | Nielsen et al. | 549/534 |
| 4,444,899 | 4/1984 | Yamada et al. | 502/355 |
| 4,459,372 | 7/1984 | Arena | 502/351 |
| 4,536,482 | 8/1985 | Carcia | 502/177 |
| 4,548,921 | 10/1985 | Gues et al. | 502/330 |
| 4,742,034 | 5/1988 | Boxhoorn et al. | 502/231 |
| 4,761,394 | 8/1988 | Lauritzen | 502/348 |
| 4,766,105 | 8/1988 | Lauritzen | 502/216 |
| 4,808,738 | 2/1989 | Lauritzen | 549/536 |
| 4,874,739 | 10/1989 | Boxhoorn | 502/218 |
| 4,897,498 | 1/1990 | Monnier et al. | 549/534 |
| 4,908,343 | 3/1990 | Bhasin | 502/218 |
| 5,037,794 | 8/1991 | Magistro | 502/355 |
| 5,055,442 | 10/1991 | Osaka et al. | 502/439 |
| 5,057,481 | 10/1991 | Bhasin | 502/208 |
| 5,063,195 | 11/1991 | Jin et al. | 502/348 |
| 5,081,096 | 1/1992 | Monnier et al. | 502/348 |
| 5,100,859 | 3/1992 | Gerdes et al. | 502/439 |
| 5,102,848 | 4/1992 | Soo et al. | 502/218 |

FOREIGN PATENT DOCUMENTS 4363139A 6/1991 Japan.
1325715 8/1973 United Kingdom.

*Primary Examiner*—Anthony McFarlane
*Attorney, Agent, or Firm*—Pamela J. McCollough

[57] ABSTRACT

This invention relates to an ethylene oxide catalyst which contains silver and one or more alkali metal promoters supported an a carrier having a crush strength of at least about 5 pounds and a settled packing density of at least about 30 pounds/cubic foot which comprises first and second alpha alumina components with a first alpha alumina component in the form of particles having a median crystallite size of from about 0.4 to about 4 microns providing from about 95% to about 40% of the total weight of alpha alumina in the carrier and a second alpha alumina component generated in situ by a sol-gel process and providing the balance of the alpha alumina in the carrier. Titania is optionally added to the carrier.

38 Claims, No Drawings

5,380,697

ETHYLENE OXIDE CATALYST AND PROCESS

FIELD OF THE INVENTION

The invention relates to silver-containing catalysts suitable for the preparation of ethylene oxide and to the use of the catalysts for the preparation of ethylene oxide. The catalysts are prepared using a unique alpha alumina based carrier.

BACKGROUND OF THE INVENTION

Catalysts for the production of ethylene oxide from ethylene and molecular oxygen are generally supported silver catalysts. Such catalysts are typically promoted with alkali metals. The use of small amounts of the alkali metals potassium, rubidium and cesium were noted as useful promoters in supported silver catalysts in U.S. Pat. No. 3,962,136, issued Jun. 8, 1976, and U.S. Pat. No. 4,010,115, issued Mar. 1, 1977. The use of other co-promoters, such as rhenium, or rhenium along with sulfur, molybdenum, tungsten and chromium is disclosed in U.S. Pat. No. 4,766,105, issued Aug. 23, 1988, and U.S. Pat. No. 4,808,738, issued Feb. 28, 1989. U.S. Pat. No. 4,908,343, issued Mar. 13, 1990, discloses a supported silver catalyst containing a mixture of a cesium salt and one or more alkali metal and alkaline earth metal salts.

The use of alumina-based catalyst carriers has been previously described in a number of patents such as, for example, U.S. Pat. No. 5,100,859, issued Mar. 31, 1992, U.S. Pat. No. 5,055,442, issued Oct. 8, 1991, U.S. Pat. No. 5,037,794, issued Aug. 6, 1991, and U.S. Pat. No. 4,874,739, issued Oct. 17, 1989. These alumina carriers have a wide variety of potential applications in the catalytic field and are especially useful where the alumina base is alpha alumina and the application is one in which abrasion resistance is a desirable feature.

SUMMARY OF THE INVENTION

This invention relates to a catalyst suitable for the production of ethylene oxide from ethylene and molecular oxygen in the vapor phase which catalyst comprises a catalytically effective amount of silver and a promoting amount of alkali metal supported on an alpha alumina based carrier having a crush strength of at least about 5 pounds and a settled packing density of at least about 30 pounds/cubic foot which comprises first and second alpha alumina components with a first alpha alumina component in the form of particles having a median crystallite size of from about 0.4 to about 4 microns providing from about 95% to about 40% of the total weight of alpha alumina in the carrier and a second alpha alumina component generated in situ by a sol-gel process and providing the balance of the alpha alumina in the carrier.

It has been found that catalysts having this unique alumina carrier have improved selectivities and/or activities over catalysts having conventional alumina carriers. These catalysts also have improved selectivity stabilities and/or activity stabilities.

DESCRIPTION OF THE PREFERRED EMBODIMENTS

The catalysts of the present invention comprise a catalytically effective amount of silver and a promoting amount of alkali metal supported on a novel alpha alumina carrier. Descriptions of the carrier, the catalyst prepared with the carrier and the use of the catalyst are provided in detail below.

THE CARRIER

The catalyst carrier in the present invention is a novel alpha alumina based catalyst carrier having a crush strength, (as measured on a Compton Tensile Tester, model 50-OP), of at least 5 pounds and a settled packing density, (as measured by ASTM D-4699-87, modified by the use of a cylinder with an inside diameter of 3¾ inches and a length of 18 inches), of at least about 30 pounds/cubic foot, preferably at least about 35 pounds/cubic foot, and more preferably at least about 38 pounds/cubic foot, which comprises first and second alpha alumina components with a first alpha alumina component in the form of particles having a median crystallite size of from about 0.4 to about 4 microns providing from about 95% to about 40%, preferably from about 95% to about 65% of the total weight of alpha alumina in the carrier and, and a second alpha alumina component generated in situ by a sol-gel process and providing the balance of the alpha alumina in the carrier.

As used herein, the term "sol-gel process" refers to a process which comprises heating an alumina sol and/or gel (i.e., hydrated alumina) to a temperature which converts at least a portion of the alumina sol and/or gel to an alumina having the corundum crystalline structure (i.e., a hexagonal close-packed structure). Temperatures of at least about 400° C., preferably above about 1100° C., and more preferably from about 1100° C. to about 1500° C., are generally used for the conversion.

The catalyst carrier is prepared by a process which comprises:
  a) forming a mixture comprising:
    i) at least one alpha alumina component with a median particle size of from about 3 to about 8 microns and;
    ii) a hydrated precursor of alpha alumina in an amount sufficient to provide from about 5% by weight to about 60% by weight of the total weight of alpha alumina in the catalyst carrier product;
    iii) from about 5% by weight to about 40%, based on the weight of the alpha alumina, of a burnout material; and
    iv) water in sufficient quantity to extrude the above mixture;
  b) extruding the mixture into the desired shapes; and
  c) firing to convert the precursor of alpha alumina to alpha alumina so as to produce a catalyst carrier in which alpha alumina particles with a median particle size of from about 3 to about 8 microns are dispersed in a matrix of alpha alumina derived from the precursor material.

The catalyst carrier may be composited with a number of alpha alumina constituents chosen to contribute to the desired physical properties, including porosity, pore volume, crush strength and the like. Often a combination of two different alpha aluminas is preferred, with a first constituent having larger particles mixed with a second constituent having smaller particles, in weight ratios of from about 10:90 to about 90:10. The first constituent typically comprises from about 10% by weight to about 90% by weight, preferably from about 40% by weight to about 80% by weight of the first alpha alumina component, and the second constituent typically comprises from about 10% by weight to about 90% by weight, preferably from about 20% by weight to about 60% by weight of the first alpha alumina component. The objective of this is to end up with a surface area in the final calcined carrier of from about 0.4 to about 5 square meters per gram ($m^2/g$). As used herein, "surface area" is used to refer to the BET surface area measured using nitrogen or krypton as the adsorbed gas. The surface area in the finished carrier is somewhat less than for the free alumina particles. Thus, a convenient mixture may comprise, for example, two types of alpha alumina particles, the first having a surface area of about 0.9 $m^2/g$ to about 1.4 $m^2/g$ and preferably about 1 $m^2/g$, a median particle size of from about 2 microns to about 4 microns and preferably about 3 microns to about 3.4 microns and a median crystallite size of from about 1.6 microns to about 2.2 microns; and the second having a surface area of about 3 $m^2/g$ to about 5 $m^2/g$, a median particle size of from about 4 microns to about 8 microns, and a median crystallite size of from about 0.4 micron to about 0.8 micron.

The hydrated precursor of alpha alumina is preferably based on a monohydrate such as boehmite, but good results are also obtained if the precursor comprises a mixture of boehmite with an aluminum trihydrate such as gibbsite or bayerite. Where such a mixture is used it is often preferred to use a weight ratio of the monohydrate, (boehmite), to trihydrate of from about 1:10 to about 1:3 and more preferably from about 1:8 to about 1:4. When the precursor of alpha alumina contains alumina trihydrate, it typically contains from about 10% by weight to about 35% by weight of alumina trihydrate, based on the total weight of alpha alumina in the carrier. Although other alumina trihydrates can be utilized, the alumina trihydrate most frequently utilized is gibbsite having a median particle size of from about 4 to about 20 microns.

In a preferred embodiment, the hydrated precursor of alpha alumina is seeded. The seed used can be any material that is effective to produce nucleation sites in the precursor so as to reduce the transition temperature at which a transition alumina converts to alpha alumina. Seeds that accomplish this goal generally have the same crystal lattice type as alpha alumina itself and lattice dimensions that do not differ by too much from those of alpha alumina. Clearly the most convenient seed is alpha alumina itself and sub-micron sized particles of alpha alumina are the preferred seed. In a preferred embodiment, the alpha alumina seed has a median particle size of less than about 0.1 micron, and comprises from about 0.2% by weight to about 5% by weight based on the total weight of alumina, measured as alpha alumina, in the catalyst carrier. It is however possible to use other seeds such as alpha ferric oxide and chromium oxide and certain complex oxides of titanium.

The alpha alumina formed from the seeded precursor when the extruded mixture is fired generally has a much finer crystal size than the alpha alumina particles with which the seeded precursor is mixed unless, during firing, it is maintained at a high temperature for a prolonged period. As produced, the seeded sol-gel material has a submicron crystal structure, but if it is held at temperatures over 1400° C. for extended periods, crystal growth begins and the size differentiation may become less apparent.

The final calcined carrier preferably has a porosity of at least 50% and more desirably from about 60% to about 75%, a crush strength of at least about 5 pounds, and a settled packing density of at least about 35 pounds per cubic foot, preferably at least about 38 pounds per cubic foot. The surface area of the final calcined carrier is preferably from about 0.4 $m^2/g$ to about 5 $m^2/g$, and more preferably from about 0.6 $m^2/g$ to about 1.2 $m^2/g$.

It is often found advantageous to add titania to the mixture to be extruded in an amount that represents from about 0.05% to about 1%, preferably from about 0.05% to about 0.5%, more preferably from about 0.08% to about 0.40%, and most preferably, from about 0.08% to about 0.25%, of the weight of the fired carrier. Certain forms of alumina and bond material may also contain titania as impurities or components. The contribution of such forms of titania are not included in the amounts specified above. The titania can be added as the dioxide, as a titanate or as a precursor of titania. In the following description, all of the above options are understood to be included under the term "titania". It is believed that the titania may function as a form of crystal growth inhibitor in the alpha alumina formed as a result of the conversion of the seeded precursor. It may be anticipated therefore that other such materials such as, for example, zirconia or magnesia, which can act in this capacity might have utility as replacements for titania. It is believed that complex solid state reactions between alumina/bond, impurities and titania added to the carrier occur and result in increased strength and density of the carrier.

The titania is preferably in the form of a powder with a relatively high surface area, i.e., at least about 8 $m^2/g$, and preferably from about 8 $m^2/g$ to about 300 $m^2/g$. In practice, the preferred titanias have an amorphous or anatase structure. While not wishing to be bound by any theory, it is believed that the rutile structure of titania does not generally show the advantages which can be obtained with the amorphous and anatase structures of titania because it typically has a much smaller surface area. Commercial pigment grades of titania can also give good results.

The carrier alumina components are then typically mixed with a burnout and/or binding agent and water, formed into shapes and calcined.

The burnout agent is a material that is added to the mixture such that upon calcination, it is completely removed from the carrier, leaving a controlled porosity in the carrier. These materials are carbonaceous materials such as coke, carbon powders, graphite, powdered plastics such as polyethylene, polystyrene and polycarbonate, rosin, cellulose and cellulose based materials, sawdust and other plant materials such as ground nut shells, e.g. pecan, cashew, walnut and filbert shells. Carbon-based burnout agents can also serve as binding agents. The burnout agents are provided in an amount and size distribution to provide a final carrier having a water pore volume (water absorption) ranging from about 0.2 to about 0.6 cc/g, preferably 0.3 to 0.5 cc/g. The burnout agents typically comprise from about 5% by weight to about 40% by weight, based on the weight of alpha alumina in the carrier. Preferred burnout agents are cellulose-derived materials, such as ground nut shells.

The term "binding agent" as used herein refers to an agent that holds together that various components of the carrier after they have been shaped into the final form, say by extrusion or pelleting. These binding agents allow the shaped materials to be dried and calcined without crumbling. Such binding agents are usually "sticky" organic materials such as polyvinyl alcohols or cellulosic materials. Binding agents may also serve as extrusion aids. In certain cases peptizing acids may be used in lieu of binding agents.

While it would appear that the alpha alumina formed from the seeded precursor acts in some sense as a matrix binder holding the rest of the alpha alumina particles together, it is usually preferred to add a ceramic bond material to the mixture to give added strength to the fired carrier. The ceramic bond material is typically present in an amount of from about 1% by weight to about 3% by weight based on the total weight of the alumina components, expressed as alpha alumina. Conventional ceramic bond materials can be used and after firing these typically comprise components, (expressed as the oxides), such as silica, alumina, alkali metal oxides, alkaline earth metal oxides, iron oxide and titanium oxide, with the first two being the dominant components. In a preferred embodiment, the ceramic bond comprises the following components, expressed as the oxides, in the following approximate proportions: 60% wt. silica, 29% wt. alumina, 3% wt. calcium oxide, 2% magnesia, 4% wt. alkali metal oxides and less than 1% wt. each of ferric oxide and titania.

After the components of the carrier are mixed together, say by mulling, the mixed material is extruded into shaped pellets, for example, cylinders, rings, trilobes, tetralobes and the like. "Extrusion aids" such as Vaseline TM Petroleum Jelly and other organic lubricating materials may be used to facilitate extrusion. The extruded material is dried to remove water that could convert to steam during calcination and destroy the extrudate shapes. After drying to a low water content, i.e., less than about 2%, the extruded material is calcined under conditions sufficient to remove burnout agents, extrusion aids, and binding agents and to fuse the alpha alumina particles into a porous, hard mass. Calcination is typically carded out in an oxidizing atmosphere, say oxygen gas or preferably air and at a maximum temperature greater than about 1300° C. and preferably ranging from about 1350° C. to about 1500° C. Times at these maximum temperatures typically range from about 0.1 to 10 hours, preferably from about 0.5 to 5 hours.

The calcined carriers and catalysts made therefrom will typically have pore volumes (water) ranging from about 0.2 to about 0.6 cc/g, preferably from about 0.3 to about 0.5 cc/g and surface areas ranging from about 0.15 to about 3 m$^2$/g, preferably from about 0.3 to about 2 m$^2$/g.

The carrier formulation preferably has a low soda content which is less than about 0.06% by weight. In practice it is very difficult to obtain a sodium-free formulation and soda contents from about 0.02 to 0.06% by weight are usually found acceptable.

The carriers described above are particularly suited for preparing ethylene oxide catalysts which have high initial selectivities.

THE CATALYST

The catalysts of the present invention comprise a catalytically effective amount of silver and a promoting amount of alkali metal(s) deposited on a carrier having a crush strength, (as measured on a Compton Tensile Tester, model 50-OP), of at least about 5 pounds and a settled packing density, (as measured by ASTM D-4699-87, modified by the use of a cylinder with an inside diameter of 3 and ¾ inches and a length of 18 inches), of at least about 35 pounds/cubic foot which comprises first and second alpha alumina components with a first alpha alumina component in the form of particles having an average crystallite size of from about 0.4 to about 4 microns providing from about 95% to about 65% of the total weight of alpha alumina in the carrier and, and a second alpha alumina component generated in situ by a sol-gel process and providing the balance of the alpha alumina in the carrier. Other promoters in promoting amounts may be optionally present such as rare earths, magnesium, rhenium and rhenium co-promoters selected from sulfur, chromium, molybdenum, tungsten and mixtures thereof.

In general, the catalysts of the present invention are prepared by impregnating porous refractory supports comprising alpha alumina with silver ions or compound(s), complex(es) and/or salt(s) dissolved in a suitable solvent sufficient to cause deposition on the support of from about 1 to about 40, preferably from about 1 to about 30 percent by weight, basis the weight of the total catalyst, of silver. The impregnated support is then separated from the solution and the deposited silver compound is reduced to metallic silver. Also deposited on the support either prior to, coincidentally with, or subsequent to the deposition of the silver will be suitable ions, or compound(s) and/or salt(s) of alkali metal dissolved in a suitable solvent. Also deposited on the carrier coincidentally with the deposition of the silver and/or alkali metal will be suitable optional promoter compound(s), complex(es) and/or salt(s) dissolved in an appropriate solvent.

The catalysts of the present invention are prepared by a technique in which the alkali metal promoter as well as any additional promoters in the form of soluble salts and/or compounds are deposited on the catalyst and/or support prior to, simultaneously with, or subsequent to the deposition of the silver and each other. The preferred method is to deposit silver and alkali metal simultaneously on the support, that is, in a single impregnation step, although it is believed that the individual or concurrent deposition of the alkali metal prior to and/or subsequent to the deposition of the silver would also produce suitable catalysts.

Promoting amounts of alkali metal or mixtures of alkali metal are deposited on a porous support using a suitable solution. Although alkali metals exist in a pure metallic state, they are not suitable for use in that form. They are used as ions or compounds of alkali metals dissolved in a suitable solvent for impregnation purposes. The carrier is impregnated with a solution of alkali metal promoter ions, salt(s) and/or compound(s) before, during or after impregnation of the silver ions or salt(s), complex(es), and/or compound(s) has taken place. An alkali metal promoter may even be deposited on the carrier after reduction to metallic silver has taken place. The promoting amount of alkali metal utilized will depend on several variables, such as, for example, the surface area and pore structure and surface chemical properties of the carrier used, the silver content of the catalyst and the particular ions used in conjunction with the alkali metal cation, optional co-promoters. The amount of alkali metal promoter deposited upon the support or present on the catalyst generally lies between about 10 parts per million and about 3000 parts per million, preferably between about 15 parts per million and about 2000 parts per million and more preferably, between about 20 parts per million and about 1500 parts per million by weight of total catalyst. Most preferably, the amount ranges between about 50 parts per million and about 1000 parts per million by weight of the total catalyst. The degree of benefit obtained within the above-defined limits will vary depending upon particular properties and characteristics, such as, for example, reaction conditions, catalyst preparative techniques, surface area and pore structure and surface chemical properties of the carrier utilized, silver content of the catalyst, and other compounds, cations or anions present in addition to alkali metal ions, and the above-defined limits were selected to cover the widest possible variations in properties and characteristics. The effects of these variation in properties are readily determined by experimentation. The alkali metal promoters are present on the catalysts in the form of cations (ions) or compounds of complexes or surface compounds or surface complexes rather than as the extremely active free alkali metals, although for convenience purposes in this specification and claims they are referred to as "alkali metal" or "alkali metal promoters" even though they are not present on the catalyst as metallic elements. For purposes of convenience, the amount of alkali metal deposited on the support or present on the catalyst is expressed as the metal. Without intending to limit the scope of the invention, it is believed that the alkali metal compounds are oxidic compounds. More particularly, it is believed that the alkali metal compounds are probably in the form of mixed surface oxides or double surface oxides or complex surface oxides with the aluminum of the support and/or the silver of the catalyst, possibly in combination with species contained in or formed from the reaction mixture, such as, for example, chlorides or carbonates or residual species from the impregnating solution(s).

In a preferred embodiment, at least a major proportion (greater than 50% wt.) of the alkali metals are selected from the group consisting of potassium, rubidium, cesium, and mixtures thereof. As used herein, the term "alkali metal" and cognates thereof refers to the alkali metals selected from the group consisting of lithium, sodium, potassium, rubidium, cesium and mixtures thereof. As used herein, the term "mixtures of alkali metals" or cognates of these terms refers to the use of two or more of the alkali metals, as appropriate, to provide a promoting effect. Non-limiting examples include cesium plus rubidium, cesium plus potassium, cesium plus sodium, cesium plus lithium, cesium plus rubidium plus sodium, cesium plus potassium plus sodium, cesium plus lithium plus sodium, cesium plus rubidium plus potassium plus sodium, cesium plus rubidium plus potassium plus lithium, cesium plus potassium plus lithium and the like. A preferred alkali metal promoter is cesium. A particularly preferred alkali metal promoter is cesium plus at least one additional alkali metal. The additional alkali metal is preferably selected from sodium, lithium and mixtures thereof, with lithium being preferred.

It should be understood that the amounts of alkali metal promoters on the catalysts are not necessarily the total amounts of these metals present in the catalyst. Rather, they are the amounts of alkali metal promoters which have been added to the catalyst by impregnation with a suitable solution of ions, salts and/or compounds and/or complexes of alkali metals. These amounts do not include amounts of alkali metals which are locked into the support, for example, by calcining, or are not extractable in a suitable solvent such as water or lower alkanol or amine or mixtures thereof and do not provide a promoting effect. It is also understood that a source of the alkali metal promoter ions, salts and/or compounds used to promote the catalyst may be the carrier. That is, the carrier may contain extractable amounts of alkali metal that can be extracted with a suitable solvent, such as water or lower alkanol, thus preparing an impregnating solution from which the alkali metal ions, salts and/or compounds are deposited or redeposited on the support.

The catalyst may also contain moderating amounts of chloride for purposes of enhancing the startup procedure for the catalysts. When chloride is added to the catalyst, the carrier can be impregnated with a solution of chloride moderator ions, salt(s) and/or compound(s) before, during or after impregnation of the silver ions or salt(s), complex(es), and/or compound(s) has taken place and before, during or after impregnation of the promoter ions or salt(s), complex(es), and/or compound(s) has taken place. The chloride moderator may even be deposited on the carrier after reduction to metallic silver has taken place. Suitable chloride-containing salts used to prepare the impregnating solutions include promoter chlorides such as lithium chloride, sodium chloride, potassium chloride, rubidium chloride and cesium chloride as well as ammonium chloride. Ammonium chloride is a preferred salt for use in preparing the chloride-containing impregnating solutions. Other compounds which decompose to the chloride ion upon processing of the catalyst are also suitable. The chloride-containing impregnating solutions will normally contain at least a small amount of water to enhance solubility of the chloride-containing salt or compound. Other promoters and co-promoters can be used in conjunction with the silver and alkali metal promoters.

Non-limiting examples of other promoters include rhenium, sulfate, molybdate, tungstate and chromate (see U.S. Pat. No. 4,766,105, issued Aug. 23, 1988); sulfate anion, fluoride anion, oxyanions of Groups 3b to 6b (see U.S. Pat. No. 5,102,848, issued Apr. 7, 1992); (i) oxyanions of an element selected from Groups 3 through 7b and (ii) alkali(ne) metal salts with anions of halides, and oxyanions selected from Groups 3a to 7a and 3b through 7b (see U.S. Pat. No. 4,908,343, issued Mar. 13, 1990).

As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counterions. The term "oxidic" refers to a charged or neutral species wherein an element in question is bound to oxygen and possibly one or more different elements by surface and/or chemical bonding, such as ionic and/or covalent and/or coordinate bonding. Thus, an oxidic compound is an oxygen-containing compound which also may be a mixed, double or complex surface oxide. Illustrative oxidic compounds include, by way of non-limiting examples, oxides (containing only oxygen as the second element), hydroxides, nitrates, sulfates, carboxylates, carbonates, bicarbonates, oxyhalides, etc. as well as surface species wherein the element in question is bound directly or indirectly to an oxygen either in the substrate or the surface.

As used herein, the term "promoting amount" of a certain component of a catalyst refers to an amount of that component which works effectively to provide an improvement in one or more of the catalytic properties of that catalyst when compared to a catalyst not containing said component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced and may even be diminished. It is further understood that different catalytic properties may be enhanced at different operation conditions. For example, a catalyst having enhanced selectivity at one set of operating conditions may be operated at a different set of conditions wherein the improvement shows up in the activity rather that the selectivity and an operator of an ethylene oxide plant will intentionally change the operation conditions in order to take advantage of certain catalytic properties even at the expense of other catalytic properties in order to maximize profits by taking into account feedstock costs, energy costs, by-product removal costs and the like.

As used herein, the term "catalytically effective amount of silver" refers to an amount of silver that provides a measurable conversion of ethylene and oxygen to ethylene oxide.

Generally, the carrier is contacted with a silver salt, a silver compound, or a silver complex which has been dissolved in an aqueous solution, so that the carrier is impregnated with said aqueous solution; thereafter the impregnated carrier is separated form the aqueous solution, e.g., by centrifugation or filtration and then dried. The thus obtained impregnated carrier is heated to reduce the silver to metallic silver. It is conveniently heated to a temperature in the range of from about 50° C. to about 600° C., during a period sufficient to cause reduction of the silver salt, compound or complex to metallic silver and to form a layer of finely divided silver, which is bound to the surface of the carrier, both the exterior and pore surface. Air, or other oxidizing gas, reducing gas, an inert gas or mixtures thereof may be conducted over the carrier during this heating step.

There are several known methods to add the silver to the carrier or support. The carrier may be impregnated with an aqueous solution containing silver nitrate dissolved therein, and then dried, after which drying step the silver nitrate is reduced with hydrogen or hydrazine. The carrier may also be impregnated with an ammoniacal solution of silver oxalate or silver carbonate, and then dried, after which drying step the silver oxalate or silver carbonate is reduced to metallic silver by heating, e.g., to about 600° C. Specific solutions of silver salts with solubilizing and reducing agents may be employed as well, e.g., combinations of the vicinal alkanolamines, alkyldiamines and ammonia. One such example of a solution of silver salts comprises an impregnating solution comprising a silver salt of a carboxylic acid, an organic amine solubilizing/reducing agent, and an aqueous solvent.

Suitable silver salts include silver carbonate and the silver salts of mono- and polybasic carboxylic and hydroxycarboxylic acids of up to about 16 carbon atoms. Silver carbonate and silver oxalate are particularly useful silver salts, with silver oxalate being most preferred.

An organic amine solubilizing/reducing agent is present in the impregnating solution. Suitable organic amine silver-solubilizing/reducing agents include lower alkylenediamines of from 1 to 5 carbon atoms, mixtures of a lower alkanolamine of from 1 to 5 carbon atoms with a lower alkylenediamine of from 1 to 5 carbon atoms, as well as mixtures of ammonia with lower alkanolamines or lower alkylenediamines of from 1 to 5 carbons. Four groups of organic amine solubilizing/reducing agents are particularly useful. The four groups include vicinal alkylenediamines of from 2 to 4 carbon atoms, mixtures of (1) vicinal alkanolamines of from 2 to 4 carbon atoms and (2) vicinal alkylenediamines of from 2 to 4 carbon atoms, mixtures of vicinal alkylenediamines of from 2 to 4 carbon atoms and ammonia, and mixtures of vicinal alkanolamines of from 2 to 4 carbon atoms and ammonia. These solubilizing/reducing agents are generally added in the amount of from about 0.1 to about 10 moles per mole of silver present.

Particularly preferred solubilizing/reducing agents are ethylenediamine, ethylenediamine in combination with ethanolamine, ethylenediamine in combination with ammonia, and ethanolamine in combination with ammonia, with ethylenediamine being most preferred. Ethylenediamine in combination with ethanolamine gives comparable results.

When ethylenediamine is used as the sole solubilizing/reducing agent, it is necessary to add amounts of the amine in the range of from about 0.1 to about 5.0 moles of ethylenediamine per mole of silver.

When ethylenediamine and ethanolamine together are used as the solubilizing/reducing agent, it is suitable to employ from about 0.1 to about 3.0 moles of ethylenediamine per mole of silver and from about 0.1 to about 2.0 moles of ethanolamine per mole of silver.

When ethylenediamine or ethanolamine is used with ammonia, it is generally useful to add at least about two moles of ammonia per mole of silver and very suitable to add from about 2 to about 10 moles of ammonia per mole of silver. The amount of ethylenediamine or ethanolamine employed then is suitably from 0.1 to 2.0 moles per mole of silver.

One method of preparing the silver containing catalyst can be found in U.S. Pat. No. 3,702,259, issued Nov. 7, 1972, incorporated by reference herein. Other methods for preparing the silver-containing catalysts which in addition contain higher alkali metal promoters can be found in U.S. Pat. No. 4,010,115, issued Mar. 1, 1977; and U.S. Pat. No. 4,356,312, issued Oct. 26, 1982; U.S. Pat. No. 3,962,136, issued Jun. 8, 1976 and U.S. Pat. No. 4,012,425, issued Mar. 15, 1977, all incorporated by reference herein. Methods for preparing silver-containing catalysts containing higher alkali metal and rhenium promoters can be found in U.S. Pat. No. 4,761,394, issued Aug. 2, 1988, which is incorporated by reference herein, and methods for silver-containing catalysts containing higher alkali metal and rhenium promoters and a rhenium co-promoters can be found in U.S. Pat. No. 4,766,105, issued Aug. 2, 1988, which is incorporated herein by reference. Methods for preparing silver-containing catalysts with a variety of different promoters are found in U.S. Pat. Nos. 4,908,343, issued Mar. 13, 1990 and 5,057,481, issued Oct. 15, 1991, both incorporated herein by reference.

A particularly preferred process of impregnating the carrier consists of impregnating the carrier with an aqueous solution containing a silver salt of a carboxylic acid, an organic amine and a salt of cesium dissolved therein. Silver oxalate is a preferred salt. It can be prepared by reacting silver oxide (slurry in water) with (a) a mixture of ethylenediamine and oxalic acid, or (b) oxalic acid and then ethylenediamine, which latter is preferred, so that an aqueous solution of silver oxalate-ethylenediamine complex is obtained, to which solution is added a certain amount of cesium compound and ammonium chloride. While addition of the amine to the silver oxide before adding the oxalic acid is possible, it is not preferred since it can give rise to solutions which are unstable or even explosive in nature. Other alia-mines and other amines, such as ethanolamine, may be added as well. A cesium-containing silver oxalate solution may also be prepared by precipitating silver oxalate from a solution of cesium oxalate and silver nitrate and rinsing with water or alcohol the obtained silver oxalate in order to remove the adhering cesium salt until the desired cesium content is obtained. The cesium-containing silver oxalate is then solubilized with ammonia and/or an amine in water. Rubidium-, potassium-, sodium-, lithium- and mixtures of alkali metal-containing solutions may be prepared also in these ways. The impregnated carriers are then heated to a temperature between about 50° C. and about 600° C., preferably between about 75° C. and about 400° C. to evaporate the liquid and produce a metallic silver.

In general terms, the impregnation process comprises impregnating the support with one or more solutions comprising silver, alkali metal and optional other promoters. As used in the instant specification and claims, the terminology "impregnating the support with one or more solutions comprising silver, alkali metal, and optional other promoters" and similar or cognate terminology means that the support is impregnated in a single or multiple impregnation with one solution containing silver, alkali metal, and optional other promoters in differing amounts; or in multiple impregnations with two or more solutions, wherein each solution contains at least one component selected from silver, alkali metal, and optional other promoter(s), with the proviso that all of the components of silver and alkali metal will individually be found in at least one of the solutions. The concentration of the silver (expressed as the metal) in the silver-containing solution will range from about 1 g/l up to the solubility limit when a single impregnation is utilized. The concentration of the alkali metal (expressed as the metal) will range from about $1 \times 10^{-3}$ g/l up to about 12 g/l and preferably, from about $10 \times 10^{-3}$ g/l to about 12 g/l when a single impregnation step is utilized. Concentrations selected within the above noted ranges will depend upon the pore volume of the catalyst, the final amount desired in the final catalyst and whether the impregnation is single or multiple. Appropriate concentrations can be readily determined by routine experimentation.

It is observed that independent of the form in which the silver is present in the solution before precipitation on the carrier, the term "reduction to metallic silver" is used, while in the meantime often decomposition by heating occurs. We prefer to use the term "reduction", since $Ag^+$ ion is converted into a metallic Ag atom. Reduction times may generally vary from about 0.5 minute to about 8 hours, depending on the circumstances.

THE PROCESS

In commercial operation, ethylene and oxygen are converted to ethylene oxide in an ethylene oxide reactor which comprises a large fixed tube heat exchanger containing several thousand tubes filled with catalysts. A coolant is used on the shell side of the reactor to remove the heat of reaction. Coolant temperatures are frequently utilized as an indication of catalyst activity, with high coolant temperatures corresponding to lower catalyst activities.

In the reaction of ethylene oxide with oxygen to produce ethylene oxide, the ethylene is typically present in at least a double amount (on a molar basis) compared with oxygen, but the amount of ethylene employed is generally much higher. The conversion is therefore conveniently calculated according to the mole percentage of oxygen which has been consumed in the reaction to form ethylene oxide and any oxygenated by-products. The oxygen conversion is dependent on the reaction temperature, and the reaction temperature is a measure of the activity of the catalyst employed. The value $T_{40}$ indicates the temperature at 40 percent oxygen conversion in the reactor and the value T is expressed in ° C. This temperature for any given catalyst is higher when the conversion of oxygen is higher. Moreover, this temperature is strongly dependent on the employed catalyst and the reaction conditions. The selectivity (to ethylene oxide) indicates the molar amount of ethylene oxide in the reaction product compared with the total molar amount of ethylene converted. In this specification, the selectivity is indicated as $S_{40}$, which means the selectivity at 40 percent oxygen conversion.

The conditions for carrying out such an oxidation reaction in the presence of the silver catalysts according to the present invention broadly comprise those already described in the prior art. This applies, for example, to suitable temperatures, pressures, residence times, diluent materials such as nitrogen, carbon dioxide, steam, argon, methane or other saturated hydrocarbons, to the presence of moderating agents to control the catalytic action, for example, 1-2-dichloroethane, vinyl chloride, ethyl chloride or chlorinated polyphenyl compounds, to the desirability of employing recycle operations or applying successive conversions in different reactors to increase the yields of ethylene oxide, and to any other special conditions which may be selected in processes for preparing ethylene oxide. Pressures in the range of from atmospheric to about 500 psig are generally employed. Higher pressures, however, are not excluded. Molecular oxygen employed as reactant can be obtained from conventional sources. The suitable oxygen charge may consist essentially or relatively pure oxygen, a concentrated oxygen stream comprising oxygen in major amount with lesser amounts of one or more diluents, such as nitrogen and argon, or another oxygen-containing stream, such as air. It is therefore evident that the use of the present silver catalysts in ethylene oxide reactions is in no way limited to the use of specific conditions among those which are known to be effective. For purposes of illustration only, the following table shows the range of conditions that are often used in current commercial ethylene oxide reactor units and which are also suitable for the instant process.

TABLE I

| *GHSV | 1500-10,000 |

TABLE I-continued

| Inlet Pressure | 150–400 psig |
|---|---|
| Inlet Feed | |
| Ethylene | 1–40% |
| O₂ | 3–12% |
| Ethane | 0–3% |
| Chlorohydrocarbon moderator | 0.3–50 ppmv total |
| Argon and/or methane and/or nitrogen diluent | Balance |
| Coolant temperature | 180–315° C. |
| Catalyst temperature | 180–325° C. |
| O₂ conversion level | 10–60% |
| EO Production (Work Rate) | 2–25 lbs. EO/cu. ft. catalyst/hr. |

*Cubic feet of gas at standard temperature and pressure passing over one cubic foot of packed catalyst per hour.

In a preferred application of the silver catalysts according to the invention, ethylene oxide is produced when an oxygen-containing gas is contacted with ethylene in the presence of the present catalysts at a temperature in the range of from about 180° C. to about ° C., and preferably a temperature in the range of from about 200° C. to about 325° C.

While the catalysts of the present invention are preferably used to convert ethylene and oxygen to ethylene oxide, olefins having no allylic hydrogens can be oxidized using the silver catalysts of the present invention to produce a high selectivity of epoxide derivatives thereof by contacting the olefin feed with an oxygen-containing gas in the presence of an organic halide and the silver catalyst described above under defined oxidation conditions.

The process for the selective epoxidation of olefins having no allylic hydrogens comprises contacting the feed olefin, preferably an olefin having at least 4 carbon atoms, with a sufficient quantity of an oxygen-containing gas so as to maintain the molar ratio of olefin to oxygen in the range of about 0.01 up to about 20, in the presence of an organic halide and a silver catalyst at a reaction pressure in the range of about 0.1 up to about 100 atmospheres and a temperature in the range of about 75° up to about 325° C. for a reaction time sufficient to obtain olefin conversions per pass in the range of about 0.1 up to about 75 mole percent.

Olefins contemplated for use in this oxidation process are those which satisfy the following structural formula:

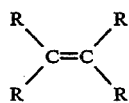

wherein each R is independently selected from the group consisting of:
(a) hydrogen,
(b) aryl and substituted aryl groups having in the range of 7 up to 20 carbon atoms,
(c) alkyl groups of the formula:

where each R' is independently:

R",

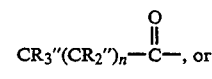

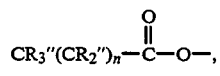

where R" is H, $C_1$—$C_{10}$ alkyl or substituted alkyl, an aryl or substituted aryl group having 6 up to 20 carbon atoms, and n is a whole number from 0–12;
(d) $CR_3''$—$(CR_2'')_x$—O—, where x is a whole number from 1–12;

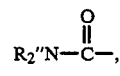

(f) $R_2''N$—;
(g) $R''S$—;
(h) $CR_2''$=$CR''$(—$CR''$=$CR''$)—y,
where y is an integer from 0–20; and

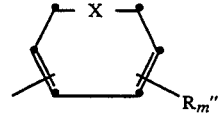

(i)

where X is O, S or NR"; and m is an integer from 0–3 with the proviso that said olefin have no allylic hydrogens and that at least one R-group not be hydrogen.

Exemplary olefins which satisfy the above structural formula include butadiene, tertiary butylethylene, vinyl furan, methyl vinyl ketone, N-vinyl pyrrolidone, and the like. A presently preferred olefin for use in the practice of this process is butadiene because of its ready availability, relatively low cost, and the wide range of possible uses for the epoxide reaction product.

The epoxides produced by this process have the structural formula:

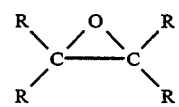

wherein each R is independently defined as set forth above. Where one or more of the R-groups contain carbon-carbon bond unsaturation, further oxidation can be carried out, thereby producing polyepoxide products.

The process is carded out by contacting the olefin to be oxidized with molecular oxygen and an organic halide under oxidation conditions, i.e. in the presence of sufficient quantities of an oxygen-containing gas to provide a molar ratio of olefin to oxygen in the range of about 0.01 up to about 20, and in the presence of about 0. 1 up to about 1000 parts per million (by volume of total feed) of organic halide. Preferred quantities of organic halide for use in the practice of the present invention fall within the range of about 1 up to about 100 parts per million, by volume of total feed.

While greater or lesser quantities of molecular oxygen can be employed, sufficient quantities of oxygen should be provided to insure that undesirably low levels of olefin conversion do not occur, while excessively high oxygen concentrations should be avoided to prevent the formation of explosive mixtures. Similarly, lower levels of organic halide will provide negligible effect on catalyst performance, while higher levels of organic halide would not be expected to provide any significant improvement in catalyst performance.

Suitable oxygen-containing gases include air, oxygen enriched air, substantially purified oxygen, oxygen diluted with inert gases such as $N_2$, Ar, $CO_2$, $CH_4$ and the like.

The organic halide can be added to the oxidation reaction zone in a variety of ways. For example, it can be mixed with the olefin to be oxidized and/or the oxygen-containing gas prior to contacting with the catalyst, or the organic halide can be introduced to the reaction zone separately from the feed olefin and/or the oxygen-containing gas.

Suitable reaction temperatures fall within the range of about 75° C. up to about 325° C. At lower temperatures, the reaction proceeds so slowly as to be impractical, while at higher temperatures undesirable levels of by-products, e.g. carbon dioxide, are obtained. Preferred reaction temperatures fall within the range of about 125° C. up to about 295° C.; with temperatures in the range of about 175° C. up to about 290° C. being most preferred because selectivity to the desired epoxide falls off at temperatures significantly above about 290° C. and space-time yields are undesirably low at temperatures below 175° C.

The reaction pressure can vary within wide ranges, with typical limits of about 0.1 up to about 100 atmospheres being chosen primarily as a function of safety, handling, equipment, and other practical considerations. Preferably, reaction pressure is maintained in the range of about 1 up to about 30 atmospheres.

Reaction times suitable for this process can vary within wide ranges. Generally, olefin, oxygen, organic halide and catalyst are maintained in contact for a time sufficient to obtain olefin conversions per pass in the range of about 0.1 up to about 75 mole percent. Preferred target olefin conversion levels per pass fall within the range of about 1 up to about 50 mole percent, while reaction times sufficient to obtain olefin conversion per pass in the range of about 5 up to about 30 mole percent are presently most preferred for efficient utilization of the reactor capacity.

Those of skill in the art recognize that the actual contact times required to accomplish the desired conversion levels can vary within wide ranges, depending on such factors as vessel size, olefin to oxygen ratios, the silver loading level on the catalyst, the presence or absence of any catalyst modifiers (and their loading levels), the amount of organic halide present in the reaction zone, the reaction temperature and pressure, and the like.

The process can be carried out in either batch or continuous mode. Continuous reaction is presently preferred since high reactor throughput and high purity product is obtained in this manner. The batch mode is satisfactorily employed when high volume of reactant throughput is not required, for example, for liquid phase reactions.

For continuous mode of reaction carried out in the gas phase, typical gas hourly space velocities (GHSV) fall within the range of about 100 up to 30,000 $hr^{-1}$. GHSV in the range of about 200 up to 20,000 $hr^{-1}$ are preferred, with GHSV in the range of about 300 up to 10,000 $hr^{-1}$ being most preferred because under such conditions the most desirable combination of feed olefin conversion and product selectivities are obtained.

When continuous mode of reaction is carried out in the liquid phase, typical liquid hourly space velocities (LHSV) employed will give contact times analogous to that obtained at the GHSV values given above. Most preferably, LHSV employed will fall in the range so as to produce the most desirable combination of feed olefin conversion levels and high product selectivity.

Recovery of the epoxide product produced can readily be carried out employing techniques well known by those of skill in the art. For example, where reaction is carried out in the continuous mode, unreacted starting material is initially separated from reaction products; and the desired product then isolated from the resulting product mixture by distillation, crystallization, extraction, or the like. Since the selectivity to the desired epoxide product is generally quite high, there are only small amounts of undesired reaction products from which to isolate the desired product.

Prior to use for oxidizing olefins having no allylic hydrogens, the silver catalysts (either before or after further treatment with promoter), are optionally calcined in an oxygen-containing atmosphere (air or oxygen-supplemented helium) at about 350° C. for about 4 hours. Following calcination, the silver catalysts are typically subjected to an activation treatment at a temperature in the range of about 300°-350° C. in an atmosphere initially containing about 2-5% hydrogen in an inert carrier such as helium or nitrogen. The hydrogen content of the activating atmosphere is gradually increased up to a final hydrogen concentration of about 20-25% at a controlled rate so that the activation temperature does not exceed 350° C. After the temperature is maintained for about 1 hour at a hydrogen concentration in the range of about 20-25%, catalyst is ready for use.

More detailed descriptions of the silver catalysts and their use in oxidizing olefins having no allylic hydrogens are found in U.S. Pat. Nos. 4,897,498, issued Jan. 30, 1990 and 5,081,096, issued Jan. 14, 1992, both of which are incorporated by reference herein.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The invention will be illustrated by the following illustrative embodiments which are provided for illustration only and are not intended to limit the scope of the instant invention.

ILLUSTRATIVE EMBODIMENTS

Carrier Preparation

Carrier A

The ceramic components are mixed with a burn-out material, (walnut shell flour), and boric acid for about a minute. Water and the seed component are then added, the water being added in an amount that is necessary to make the mixture extrudable. Generally this is about 30% by weight of the total solids present. The mixture is mixed for about two to four minutes and then about 5% by weight based on the weight of the ceramic components, of vaseline is added as an extrusion aid. The mixture is then mixed for a further 2 to 4 minutes before being extruded in the form of hollow cylinders and dried to less than 2% uncombined water. These were then fired in a tunnel kiln with a maximum temperature of about 1500° C. for about 4 hours. The carrier is described in terms of its formulation in Table 1 and in terms of its physical properties in Table 2.

Carrier B

Carrier B was prepared in a manner similar to Carrier A except that titania was added to the carrier formulation. The carrier is described in terms of its formulation in Table 1 and in terms of its physical properties in Table 2.

Carrier C

Carrier C was prepared in a manner similar to Carrier A except that the carrier contains no alpha alumina component generated by a sol-gel process, and no seed component, i.e., Alpha Alumina #5, was added to the carrier formulation. The carrier is described in terms of its formulation in Table 1 and in terms of its physical properties in Table 2.

Carrier D

Carrier D was prepared in a manner similar to Carrier A except that the carrier contains no alpha alumina component generated by a sol-gel process, and no seed component, i.e., Alpha Alumina #5, was added to the carrier formulation. The carrier is described in terms of its formulation in Table 1 and in terms of its physical properties in Table 2.

TABLE 1

| CARRIER COMPOSITIONS | | | | |
|---|---|---|---|---|
| | Carrier A, % wt. | Carrier B, % wt. | Carrier C, % wt. | Carrier D, % wt. |
| Alpha Alumina #1[1,2] | 46.6 | 46.6 | None | 98.8 |
| Alpha Alumina #2[1,3] | 28.0 | 28.0 | None | None |
| Alpha Alumina #3[1,4] | None | None | 74 | — |
| Alpha Alumina #4[1,5] | None | None | 25 | — |
| Alpha Alumina #5 (Seed)[1,6] | 0.9 | 0.9 | None | None |
| $TiO_2$[1] | None | 0.2 | None | None |
| $ZrO_2$[1] | None | None | None | 1 |
| Gibbsite[1,7] | 18.7 | 18.7 | None | None |
| Boehmite[1,8] | 4.5 | 4.5 | None | None |
| Ceramic Bond[1,9,11,12] | 1.3 | 1.3 | 1.0 | 0.2 |
| Organic Burnout[10] | 11.0 | 11.0 | 30 | 28 |
| Vaseline[10] | 5.0 | 5.0 | 5 | 5 |
| Boric Acid[10] | 0.15 | 0.15 | 0.1 | 0.1 |
| Water (to make extrudable)[13] | ~30 | ~30 | ~30 | ~30 |

[1]Indicates "ceramic components" and percentages given are based on 100% of the ceramic components.

[2]"Alpha Alumina #1" is an alpha alumina that had a median particle size of about 3 to about 3.4 microns, a BET surface area of about 0.9 to about 1.4 $m^2/g$, a crystallite size of about 1.6 to about 2.2 microns and a soda content of about 0.02% to about 0.06%.

[3]"Alpha Alumina #2" is an alpha alumina with a median particle size of about 4.0 to about 8.0 microns, a surface area of about 3.0 to about 5.0 $m^2/g$, a crystallite size of from about 0.4 to about 0.8 micron and a soda content of about 0.1% to about 0.3%.

[4]"Alpha Alumina #3" is an alpha alumina that had a median particle size of 3.6 to 4.2 microns, a BET surface area of about 0.8 to about 1.0 $m^2/g$, a crystallite size of 3 to 4 microns and a soda content of about 0.05%.

[5]"Alpha Alumina #4" is an alpha alumina that had a median particle size of 2.5 to 3.5 microns, a BET surface area of about 3 to about 4 $m^2/g$, a crystallite size of 3 to 4 microns and a soda content of about 0.1%.

[6]"Alpha Alumina #3" is an alpha alumina that was used as the seed for the gibbsite and boehmite precursors of alpha alumina. Its median particle size was less than 0.1 micron.

[7]The gibbsite had a median particle size of from about 4.0 to about 20 microns.

[8]The boehmite was dispersible as a sol.

[9]The ceramic bond for carriers A and B contained components, expressed as the oxides, in the following approximate proportions: 60% wt. silica, 29% wt. alumina, 3% wt. calcium oxide, 2% magnesia, 4% wt. alkali metal oxides and less than 1% wt. each of ferric oxide and titania.

[10]Percentages are based on the total weight of the ceramic components.

[11]The ceramic bond for Carrier C contained components, expressed as oxides, in the following approximate proportions: 67% wt. silica, 30% wt. alumina, about 1% wt. each of ferric oxide and titania, and a trace of alkali metal and alkaline earth oxides.

[12]The ceramic bond used for Carrier D was calcium silicate.

[13]Percentages are based on total weight of solids.

TABLE 2

| CARRIER PROPERTIES | | | | |
|---|---|---|---|---|
| | Carrier A | Carrier B | Carrier C | Carrier D |
| Water Absorption, %[1] | 44.5 | 38.3 | 46.4 | 41.5 |
| Packing Density, lbs/$ft^3$ [2] | 46.0 | 50.9 | 45 | 48.3 |
| Crush Strength, lbs[3] | 14.0 | 14.9 | 17 | 22.0 |
| Surface Area, $m^2/g$[4] | 0.97 | 1.01 | 0.51 | 0.50 |
| Acid Leachables, ppm | | | | |
| Na | 217 | 350 | 42 | 50.5 |
| K | 80 | 76 | 30 | 41 |
| Ca | 189 | 149 | n.a. | 850 |
| Al | 520 | 579 | n.a. | 534 |
| $TiO_2$, % | None | 0.2 | None | None |

TABLE 2-continued

| CARRIER PROPERTIES | | | | |
|---|---|---|---|---|
| | Carrier A | Carrier B | Carrier C | Carrier D |
| Firing Temperature, °C. | 1480 | 1450 | 1420 | 1390 |

[1]"Water Absorption" is a measure of the increase in weight of the carrier after being immersed in water and weighed.
[2]"Packing Density" is the settled packing density as measured by ASTM D-4699-87, modified by the use of cylinder with an inside diameter of 33¾ inches and a length of 18 inches, or an equivalent.
[3]"Crush Strength" is measured on a Compton Tensile Tester, model 50-OP.
[4]"Surface Area" is the BET surface area measured using nitrogen or krypton as the adsorbate.

Catalyst Preparation

The following illustrative embodiment describes preparative techniques for making the catalysts of the instant invention (Catalysts A, B, C, D, and F) and the comparative catalysts (Comparative Catalysts E and G) and the technique for measuring the properties of these catalysts.

Part A: Preparation of stock silver oxalate/ethylenediamine solution for use in catalyst preparation:

1) Dissolve 415 grams (g) of reagent-grade sodium hydroxide in 2340 milliliters (ml) deionized water. Adjust the temperature to 50° C.
2) Dissolve 1699 g of (high purity) silver nitrate in 2100 ml deionized water. Adjust the temperature to 50° C.
3) Add sodium hydroxide solution slowly to silver nitrate solution with stirring while maintaining a temperature of 50° C. Stir for 15 minutes after addition is complete, and then lower the temperature to 40° C.
4) Insert clean filter wands and withdraw as much water as possible from the precipitate created in step (3) in order to remove sodium and nitrate ions. Measure the conductivity of the water removed and add back as much fresh aleionized water as was removed by the filter wands. Stir for 15 minutes at 40° C. Repeat this process until the conductivity of the water removed is less than 90 μmho/cm. Then add back 1500 ml deionized water.
5) Add 630 g of high-purity oxalic acid dihydrate in approximately 100 g increments. Keep the temperature at 40° C. and stir to mix thoroughly. Add the last portion of oxalic acid dihydrate slowly and monitor pH to ensure that pH does not drop below 7.8.
6) Remove as much water from the mixture as possible using clean filter wands in order to form a highly concentrated silver-containing slurry. Cool the silver oxalate slurry to 30° C.
7) Add 699 g of 92 percent weight ( % w) ethylenediamine (8% deionized water). Do not allow the temperature to exceed 30° C. during addition.

The above procedure yields a solution containing approximately 27-33% w silver which provides the "stock solution" used in the preparation of Catalysts A, B, C, D and F and Comparative Catalysts E and G below.

Part B: Preparation of impregnation solutions

For Catalyst A 161.3 Grams of silver stock solution with a specific gravity of 1.543 was diluted with 4.2 grams of water and 13.5 grams of monoethanolamine. 0.0350 Grams of $NH_4F$ were dissolved in 2 cc of water and added to the silver solution. CsOH (50% solution in water) in an amount of 0.1367 grams was added to 60 grams of the above diluted silver solution and the resulting mixture was used for the carrier impregnation.

For Catalyst B 175.4 Grams of silver stock solution with a specific gravity of 1.53 was diluted with 3.6 grams of water. 0.0387 Grams of $NH_4F$ were dissolved in 2 cc of water and added to the silver solution. CsOH (50% solution in water) in an amount of 0.1536 grams was added to 60 grams of the above diluted silver solution and the resulting mixture was used for the carrier impregnation.

For Catalyst C 165.3 Grams of silver stock solution with a specific gravity of 1.55 was diluted with 13.9 grams of monoethanolamine. 0.0426 Grams of $NH_4F$ were dissolved in 2.5 grams of water and added to the silver solution. CsOH (50% solution in water) in an amount of 0.1406 grams was added to 60 grams of the above diluted silver solution and the resulting mixture was used for the carrier impregnation.

For Catalyst D 161.2 grams of silver stock solution with a specific gravity of 1.555 was diluted with 17.8 grams of water. 0.0868 Grams of $(NH_4)ReO_4$ were dissolved in 2 cc of water/EDA mixture (50/50 by weight) and added to the silver solution. CsOH (50% solution in water) in an amount of 0.1743 grams was added to 60 grams of the above diluted silver solution and the resulting mixture was used for the carrier impregnation.

For Comparative Catalyst E 129.7 Grams of silver stock solution containing 29.7% Ag was diluted with 14 grams of water and 6.3 grams of monoethanolamine. 0.0285 Grams of $NH_4F$ were dissolved in 2 cc of water and added to the silver solution. CsOH (50% solution in water) in an amount of 0.0582 grams was added to 50 grams of the above diluted silver solution and the resulting mixture was used for the carrier impregnation.

For Catalyst F 168.1 Grams of silver stock solution with a specific gravity of 1.546 was diluted with 10.9 grams of water. 0.1442 Grams of $(NH_4)ReO_4$, 0.0704 grams of $Li_2SO_4 \cdot H_2O$, 0.303 grams of $LiNO_3$ were dissolved in approximately 2.0 cc of ethylenediamine/$H_2O$ (50/50 by weight) and added to the silver solution. CsOH (50% solution in water) in an amount of 0.1985 grams was added to 50 grams of the above diluted silver solution and the resulting mixture was used for the carrier impregnation.

For Comparative Catalyst G

101 Grams of silver stock solution with a specific gravity of 1.558 was diluted with 12.9 grams of water. 0.0766 Grams of $(NH_4)ReO_4$, 0.0374 grams of $Li_2SO_4 \cdot H_2O$, 0.1616 grams of $LiNO_3$ were dissolved in approximately 2.0 grams of ethylenediamine/$H_2O$ (50/50 by weight) and added to the silver solution. CsOH (50% solution in water) in an amount of 0.111 grams was added to 50 grams of the above diluted silver solution and the resulting mixture was used for the carrier impregnation.

Part C: Catalyst Impregnation and Curing

Catalyst A

Approximately 30 g of carrier A (described above in Tables 1 and 2) is placed under 25 mm vacuum for 3 minutes at room temperature. Approximately 50 to 60 g of doped impregnating solution (as described in Part B above under "For Catalyst A") is then introduced to submerge the carrier, and the vacuum is maintained at 25 mm for an additional 3 minutes. At the end of this time, the vacuum is released, and excess impregnating solution is removed from the carrier by centrifugation for 2 minutes at 500 rpm. If the impregnating solution is prepared without monoethanolamine, then the impregnated carrier is then cured by being continuously shaken in a 300 cu. ft/hr. air stream flowing across a cross-sectional area of approximately 3–5 square inches at 240–270° C. for 3–6 minutes. If significant monoethanolamine is present in the impregnating solution, then the impregnated carrier is cured by being continuously shaken in a 300 cu. ft./hr. air stream at 250° C. to 270° C. for 4–8 minutes. The cured catalyst is then ready for testing. The properties of Catalyst A are shown in Table 3 below.

Catalyst B

Catalyst B was prepared in the same manner as Catalyst A, except that Catalyst carrier B was used in place of Catalyst carrier A and the impregnating solution used was that described In Part B above under "For Catalyst B". The properties of Catalyst B are shown in Table 3 below.

Catalyst C

Catalyst C was prepared using a double impregnation technique. In this technique 120 g of Catalyst carrier B was impregnated with 240 g of silver stock solution with a specific gravity of 1.555. The impregnated carrier was dried/roasted to decompose silver salts to metallic silver. Water pore volume was determined after the first impregnation and was used to calculate the dopant concentrations. The second impregnation was carried out with the impregnating solution described in the Part B above under "For Catalyst C". The catalyst was cured in a manner similar to that described above. The properties of Catalyst C are shown in Table 3 below.

Catalyst D

Approximately 30 g of carrier A (described above in Tables 1 and 2) is placed under 25 mm vacuum for 3 minutes at room temperature. Approximately 50 to 60 g of doped impregnating solution (as described In Part B above under "For Catalyst D") is then introduced to submerge the carrier, and the vacuum is maintained at 25 mm for an additional 3 minutes. At the end of this time, the vacuum is released, and excess impregnating solution is removed from the carrier by centrifugation for 2 minutes at 500 rpm. If the impregnating solution is prepared without monoethanolamine, then the impregnated carrier is then cured by being continuously shaken in a 300 cu. ft/hr. air stream flowing across a cross-sectional area of approximately 3–5 square inches at 240–270° C. for 3–6 minutes. If significant monoethanolamine is present in the impregnating solution, then the impregnated carrier is cured by being continuously shaken in a 300 cu. ft./hr. air stream at 250° C. to 270° C. for 4–8 minutes. The cured catalyst is then ready for testing. The properties of Catalyst D are shown in Table 3 below.

Comparative Catalyst E

Comparative Catalyst E was prepared in the same manner as Catalyst A, except that Catalyst carrier C was used in place of Catalyst carrier A and the impregnating solution used was that described in Part B above under "For Comparative Catalyst E". The properties of Comparative Catalyst E are shown in Table 3 below.

Catalyst F

Catalyst F was prepared in the same manner as Catalyst D, except that Catalyst carrier B was used in place of Catalyst carrier A and the impregnating solution used was that described in Part B above under "For Catalyst F". The properties of Catalyst F are shown in Table 3 below.

Comparative Catalyst G

Comparative Catalyst G was prepared in the same manner as Catalyst D, except that Catalyst carrier D was used in place of Catalyst carrier A and the impregnating solution used was that described in Part B above under "For Comparative Catalyst G". The properties of Comparative Catalyst G are shown in Table 3 below.

TABLE 3

| | CATALYST COMPOSITION | | |
|---|---|---|---|
| | Ag, wt % | Cs, ppm | Re, ppm |
| Catalyst A | 14.5 | 596 | None |
| Catalyst B | 14.5 | 601 | None |
| Catalyst C | 26.6 | 500 | None |
| Catalyst D | 14.5 | 752 | 186 |
| Comparative Catalyst E | 14.5 | 285 | None |
| Catalyst F | 13.5 | 699 | 279 |
| Comparative Catalyst G | 13.2 | 493 | 279 |

The actual silver content of the catalyst can be determined by any of a number of standard, published procedures. The actual level of cesium on the catalyst can be determined by employing a stock cesium hydroxide solution, which has been labeled with a radioactive isotope of cesium, in catalyst preparation. The cesium content of the catalyst can then be determined by measuring the radioactivity of the catalyst. Alternatively, the cesium content of the catalyst can be determined by leaching the catalyst with boiling deionized water. In this extraction process cesium, as well as other alkali metals, is measured by extraction from the catalyst by boiling 10 grams of whole catalyst in 20 milliliters of water for 5 minutes, repeating the above two more times, combining the above extractions and determining the amount of alkali metal present by comparison to standard solutions of reference alkali metals using atomic absorption spectroscopy (using Varian Techtron Model 1200 or equivalent). It should be noted that the cesium content of the catalyst as determined by the water leaching technique may be lower than the cesium content of the catalyst as determined by the radiotracer technique.

Part D: Standard Microreactor Catalyst Test Conditions/Procedure

A. For Catalysts A, B, C and Comparative Catalyst E 1 to 3 Grams of crushed catalyst (20–30 mesh) are loaded into a ¼ inch diameter stainless steel U-shaped tube. The U tube is immersed in a molten metal bath (heat medium) and the ends are connected to a gas flow system. The weight of the catalyst used and the inlet gas flow rate are adjusted to achieve a gas hourly space velocity of 6800. The outlet gas pressure is 210 psig.

The gas mixture passed thorough the catalyst bed (in once-through operation) during the entire test run (including startup) consists of 25% ethylene, 7% oxygen, 5% carbon dioxide, 1.25 to 5 ppmv ethyl chloride with the balance being nitrogen/argon.

The startup procedure involved ramping the temperature from 180° C. to 230° C. in the following fashion: 1 hour at 180° C, 1 hour at 190° C, 1 hour at 200° C, 1 hour 210° C, 1 hour at 220° C, 2 hours at 220° C, 2 hours at 225° C, 2 hours at the temperature was adjusted to provide 1.5% ethylene oxide at the reactor outlet. Catalyst selectivity ($S_{1.5}$) and catalyst activity ($T_{1.5}$) were measured at those conditions.

To allow meaningful comparison of the performance of catalysts tested at different times, the Catalysts A, B, C and Comparative Catalyst E were tested simultaneously with a standard reference catalyst which was $S_{1.5}=81.7\%$ and $T_{1.5}=235°$ C.

Catalysts A, B, C and Comparative Catalyst E prepared above were tested using the above procedure and the results are given in Table 4 below.

B. For Catalyst D

Catalyst D was tested in a manner similar to that described for Catalysts A, B, C and Comparative Catalyst E above, except that startup procedure is as follows. The initial reactor (heat medium) temperature is 225° C. After 3 hours under nitrogen flow at this initial temperature, the temperature is increased to 235° C. for 1 hour, followed by 245° C. for 1 hour. The temperature was then adjusted to 1.5% ethylene oxide in the reactor outlet. The results are given in Table 4 below.

TABLE 4

| CATALYST PERFORMANCE | | |
|---|---|---|
|  | $S_{1.5}$, % | $T_{1.5}$, °C. |
| Catalyst A | 82.0 | 226 |
| Catalyst B | 82.9 | 217 |
| Catalyst C | 82.0 | 220 |
| Catalyst D | 84.0 | 233 |
| Comparative Catalyst E | 81.2 | 230 |

As can be seen from Table 4, the initial selectivities of Catalysts A, B, C and D are improved over the initial selectivity of Comparative Catalyst E. It can also be seen that the initial activities of Catalysts A, B and C are improved over that of Comparative Catalyst E.

C. For Catalyst F and Comparative Catalyst G 3 to 5 Grams of crushed catalyst (14–20 mesh) are loaded into a ¼ inch diameter stainless steel U-shaped tube. The U tube is immersed in a molten metal bath (heat medium) and the ends are connected to a gas flow system. The weight of the catalyst used and the inlet gas flow rate are adjusted to achieve a gas hourly space velocity of 3300. The outlet gas pressure is 210 psig.

The gas mixture passed thorough the catalyst bed (in once-through operation) during the entire test run (including startup) consists of 30% ethylene, 8.5% oxygen, 5% carbon dioxide, 1.5 to 5 ppmv ethyl chloride with the balance being nitrogen/argon.

Prior to being contacted with the reactant gases, the catalysts are typically pretreated with nitrogen gas at 225° C. for 3 hours for all fresh catalysts and for 24 hours or longer for aged, but untested catalysts.

The initial reactor (heat medium) temperature is 225° C. After 1 hour at this initial temperature, the temperature is increased to 235° C., followed by 245° C. for 1 hour. The temperature is then adjusted so as to achieve a constant oxygen conversion of 40% ($T_{40}$). The moderator level is varied for 4–24 hours at each level to determine the optimum moderator level and at $T_{40}$ and $S_{40}$ are usually obtained when the catalyst has been onstream for a total of about 24 hours and are provided in Table 5 below. Due to slight differences in feed gas composition, gas flow rates, and the calibration of analytical instruments used to determine the feed and product gas compositions, the measured selectivity and activity of a given catalyst may vary slightly from one test run to the next.

To allow meaningful comparison of the performance of catalysts tested at different times, all catalysts described in this illustrative embodiment were tested simultaneously with a standard reference catalyst which was $S_{40}=81.0\%$ and $T_{40}=230°$ C.

Catalysts F and Comparative Catalyst G prepared above were testing using the above procedure and the results are given in Table 5 below.

TABLE 5

| CATALYST PERFORMANCE | | |
|---|---|---|
|  | $S_{40}$, % | $T_{40}$, °C. |
| Catalyst F | 87.2 | 249 |
| Comparative Catalyst G | 86.5 | 262 |

As can be seen from Table 5, the initial selectivity and the initial activity of Catalyst F is improved over the initial selectivity and the initial activity of Comparative Catalyst G.

What is claimed is:

1. A catalyst suitable for the vapor phase production of ethylene oxide from ethylene and oxygen comprising a catalytically effective amount of silver and a promoting amount of alkali metal deposited on a carrier having a crush strength of at least 5 pounds and a settled packing density of at least about 30 pounds/cubic foot which comprises first and second alpha alumina components with a first alpha alumina component in the form of particles having a median crystallite size of from about 0.4 to about 4 microns providing from about 95% to about 40% of the total weight of alpha alumina in the carrier and a second alpha alumina component generated by a sol-gel process and providing the balance of the alpha alumina in the carrier.

2. The catalyst of claim 1 wherein, in the carrier, the first alpha alumina component comprises a first constituent and a second constituent in which the first constituent provides from about 10% by weight to about 90% by weight of the first component weight in the form of particles with a median particle size of from about 2.5 microns to about 4 microns and an average crystallite size of from about 1.5 to about 2.5 microns, and the second constituent provides from about 90% by weight to about 10% by weight of the first component weight in the form of particles with a median particle size greater of from about 4 microns to about 10 microns and an average crystallite size of from about 0.4 to about 0.8 micron.

3. The catalyst of claim 1 wherein, in the carrier, the second alpha alumina component is generated by a seeded sol-gel process.

4. The catalyst of claim 3 wherein, in the carrier, the sol-gel alumina is seeded with an effective amount of sub-micron sized particles of alpha alumina seed.

5. The catalyst of claim 1 wherein the carrier further comprises from about 0.05% by weight to about 1% by weight, based on the weight of alumina in the carrier, of titania.

6. The catalyst of claim 5 wherein the titania has a surface area of at least 8 square meters per gram.

7. The catalyst of claim 1 wherein the carrier has a pore volume of from about 0.3 to about 0.6 cc/gram.

8. The catalyst of claim 1 wherein the carrier further comprises a ceramic bond material in an amount that is from about 1% by weight to about 3% by weight of the alumina components, expressed as alpha alumina.

9. The catalyst of claim 1 wherein the carrier has a crush strength of at least 5 pounds and a settled packing density of at least about 30 pounds/cubic foot which comprises first and second alpha alumina components; wherein the first alpha alumina component has two constituents including:
   a) a first constituent providing from about 40% to about 80% by weight of the first alpha-alumina component and having a median particle size of from about 2 microns to about 4 microns;
   b) a second constituent providing from about 20% to about 60% of the weight of the first alpha alumina component and having a median particle size of from about 4 to about 8 microns;
said first alpha alumina component providing from about 95% to about 65% of the total weight of alpha alumina in the carrier; and a second alpha alumina component generated in situ by a sol-gel process and providing the balance of the alpha alumina in the carrier.

10. The catalyst of claim 9 wherein the carrier further comprises from about 0.05% by weight to about 1% by weight of titania.

11. The catalyst of claim 1 wherein the silver ranges from about 1 percent by weight to about 40 percent by weight of the total catalyst and the alkali metal ranges from about 10 parts per million to about 3000 parts per million, expressed as the metal, by weight of the total catalyst.

12. The catalyst of claim 11 wherein said alkali metal promoter is selected from the group consisting of potassium, rubidium, cesium, lithium and mixtures thereof.

13. The catalyst of claim 12 wherein said promoter is cesium.

14. The catalyst of claim 1 wherein said alkali metal promoter comprises cesium plus at least one additional alkali metal.

15. The catalyst of claim 1 wherein the catalyst additionally comprises a promoting amount of rhenium.

16. The catalyst of claim 15 wherein the catalyst additionally comprises a rhenium co-promoter selected from the group consisting of sulfur, molybdenum, tungsten, chromium and mixtures thereof.

17. A catalyst suitable for the vapor phase production of ethylene oxide from ethylene and oxygen comprising a catalytically effective amount of silver and a promoting amount of alkali metal deposited on a carrier prepared by a process which comprises:
   a) forming a mixture comprising:
      i) at least one alpha alumina component with a median particle size of from 3 to about 8 microns,
      ii) a hydrated precursor of alpha alumina in an amount sufficient to provide from about 5% to about 60% by weight of the total weight of alpha alumina in the catalyst carrier,
      iii) from about 5% to about 40%, based on the weight of the alpha alumina, of a burnout material, and
      iv) water in sufficient quantity to extrude the above mixture;
   b) extruding the mixture into the desired shapes; and
   c) firing to convert the precursor of alpha alumina to alpha alumina so as to produce a catalyst carrier in which alpha alumina particles with a median particle size of from about 3 to about 8 microns are dispersed in a matrix of alpha alumina derived from the precursor material.

18. The catalyst of claim 17 wherein, in the carrier, the precursor of alpha alumina comprises a boehmite.

19. The catalyst of claim 17 wherein, in the carrier, the precursor of alpha alumina further comprises alumina trihydrate.

20. The catalyst of claim 17 wherein, in the carrier, the precursor of alpha alumina is seeded with sub-micron sized particles of alpha alumina in an amount that is from about 0.2% by weight to about 5% by weight based on the total alumina weight, measured as alpha alumina, in the catalyst carrier.

21. The catalyst of claim 17 wherein, in the carrier, from about 0.05% by weight to about 1% by weight based on the total weight of alumina in the formulation expressed as alpha alumina, of titania is added to the mixture to be extruded.

22. The catalyst of claim 17 wherein, in the carrier, a ceramic bond material is added to the extrudable mixture in an amount that is from about 1% by weight to about 3% of the weight of the alumina components, expressed as alpha alumina, in the mixture.

23. The catalyst of claim 17 wherein the silver ranges from about 1 percent by weight to about 40 percent by weight of the total catalyst and the alkali metal ranges from about 10 parts per million to about 3000 parts per million, expressed as the metal, by weight of the total catalyst.

24. The catalyst of claim 23 wherein said alkali metal promoter is selected from the group consisting of potassium, rubidium, cesium, lithium and mixtures thereof.

25. The catalyst of claim 24 wherein said promoter is cesium.

26. The catalyst of claim 17 wherein said alkali metal promoter comprises cesium plus at least one additional alkali metal.

27. The catalyst of claim 17 wherein the catalyst additionally comprises a promoting amount of rhenium.

28. The catalyst of claim 27 wherein the catalyst additionally comprises a rhenium co-promoter selected from the group consisting of sulfur, molybdenum, tungsten, chromium and mixtures thereof.

29. A catalyst suitable for the vapor phase production of ethylene oxide from ethylene and oxygen comprising a catalytically effective amount of silver and a promoting amount of alkali metal deposited on a carrier prepared by a process which comprises:
   a) forming a mixture comprising:
      i) an alpha alumina having a first component with a median particle size of from about 2 to about 4 microns and a second component with a median particle size of about 4 to about 8 microns,
      ii) a seeded, hydrated precursor of alpha alumina in an amount sufficient to provide from about 5% by weight to about 60% by weight of the total weight of alpha alumina in the catalyst carrier,
      iii) from about 5% by weight to about 40% by weight, based on the weight of the alpha alumina, of a burnout material;
      iv) from about 1% by weight to about 3 % by weight based on the weight of alumina in the composition expressed as alpha alumina, of a ceramic bond material, v) from about 0.05 % by weight to about 1% by weight, based on the total alumina weight in the mixture expressed as alpha alumina of titania, and vi) water in sufficient quantity to extrude the above mixture;

b) extruding the mixture into the desired shapes; and c) firing to convert the seeded precursor of alpha alumina to alpha alumina so as to produce a catalyst carrier in which alpha alumina particles with a particle size of from about 3 to about 8 microns are dispersed in a matrix of alpha alumina derived from the seeded precursor material.

30. The catalyst of claim 29 wherein, in the carrier, the precursor of alpha alumina comprises a boehmite.

31. The catalyst of claim 30 wherein, in the carrier, the precursor of alpha alumina further comprises from about 10% by weight to about 35% by weight of alumina trihydrate, based on the total weight of alpha alumina in the carrier.

32. The process of claim 29 wherein, in the carrier, the precursor of alpha alumina is seeded with sub-micron sized particles of alpha alumina in an amount that is from about 0.2% by weight to about 5% by weight based on the total alumina weight, measured as alpha alumina, in the catalyst carrier.

33. The catalyst of claim 29 wherein the silver ranges from about 1 percent by weight to about 40 percent by weight of the total catalyst and the alkali metal ranges from about 10 parts per million to about 3000 parts per million, expressed as the metal, by weight of the total catalyst.

34. The catalyst of claim 33 wherein said alkali metal promoter is selected from the group consisting of potassium, rubidium, cesium, lithium and mixtures thereof.

35. The catalyst of claim 34 wherein said promoter is cesium.

36. The catalyst of claim 29 wherein said alkali metal promoter comprises cesium plus at least one additional alkali metal.

37. The catalyst of claim 29 wherein the catalyst additionally comprises a promoting amount of rhenium.

38. The catalyst of claim 37 wherein the catalyst additionally comprises a rhenium co-promoter selected from the group consisting of sulfur, molybdenum, tungsten, chromium and mixtures thereof.

* * * * *